United States Patent
Howell

(10) Patent No.: US 11,497,467 B2
(45) Date of Patent: Nov. 15, 2022

(54) PROBE HEAD-COVER APPLICATOR AND METHOD THEREOF

(71) Applicant: Bard Access Systems, Inc., Salt Lake City, UT (US)

(72) Inventor: Glade H. Howell, Draper, UT (US)

(73) Assignee: Bard Access Systems, Inc., Salt Lake City, UT (US)

( * ) Notice: Subject to any disclaimer, the term of this patent is extended or adjusted under 35 U.S.C. 154(b) by 301 days.

(21) Appl. No.: 17/005,137

(22) Filed: Aug. 27, 2020

(65) Prior Publication Data

US 2021/0059639 A1 Mar. 4, 2021

Related U.S. Application Data

(60) Provisional application No. 62/894,516, filed on Aug. 30, 2019.

(51) Int. Cl.
*A61B 8/00* (2006.01)

(52) U.S. Cl.
CPC .......... *A61B 8/4422* (2013.01); *A61B 8/4281* (2013.01); *A61B 8/4444* (2013.01)

(58) Field of Classification Search
None
See application file for complete search history.

(56) References Cited

U.S. PATENT DOCUMENTS

| | | | | |
|---|---|---|---|---|
| 5,782,767 A * | 7/1998 | Pretlow, III | ......... | A61B 8/4281 |
| | | | | 600/443 |
| 10,064,599 B2 * | 9/2018 | Desai | .................. | A61B 8/4281 |
| 10,085,716 B2 * | 10/2018 | Romano | ............. | A61B 8/4281 |
| 10,507,008 B2 * | 12/2019 | Scully | .................. | A61K 49/226 |
| 10,617,386 B2 * | 4/2020 | Kitamura | ............. | A61B 8/4281 |
| 10,980,510 B2 * | 4/2021 | Scully | .................. | A61B 8/4422 |
| 2002/0068871 A1 * | 6/2002 | Mendlein | ............. | A61B 8/4209 |
| | | | | 600/459 |

(Continued)

FOREIGN PATENT DOCUMENTS

| | | | | | |
|---|---|---|---|---|---|
| CN | | 107616813 A | * | 1/2018 | |
| CN | | 108324322 A | * | 7/2018 | ......... A61B 8/4281 |
| WO | WO-2020009395 A1 | * | 1/2020 | ............. A61B 46/10 |

OTHER PUBLICATIONS

English language translation CN 108324322 A, Copyright © 2022 Clarivate Analytics. (Year: 2022).*

(Continued)

*Primary Examiner* — Colin T. Sakamoto
(74) *Attorney, Agent, or Firm* — Rutan & Tucker LLP

(57) ABSTRACT

Disclosed herein is a probe head-cover applicator and method for applying a probe-head cover to a probe head of an ultrasound probe. A probe head-cover applicator can include a tray including a cavity, an insert of a compressible material suspended over the cavity, and a probe-head cover adhered to the insert. The insert can include a first adhesive on an outward-facing surface of the insert facing away from the cavity. The probe-head cover can be adhered to the insert by the first adhesive. The probe-head cover can include a second adhesive on an outward-facing surface of the probe-head cover facing away from the insert. The second adhesive can be configured to adhere the probe-head cover to a probe head of an ultrasound probe when the probe head is inserted into the cavity.

21 Claims, 2 Drawing Sheets

(56) References Cited

U.S. PATENT DOCUMENTS

| | | | | |
|---|---|---|---|---|
| 2003/0149359 A1* | 8/2003 | Smith | ............ | A61B 8/4281 |
| | | | | 600/437 |
| 2005/0215901 A1* | 9/2005 | Anderson | ............ | A61B 8/12 |
| | | | | 600/445 |
| 2006/0264751 A1* | 11/2006 | Wendelken | ............ | A61B 8/4281 |
| | | | | 601/1 |
| 2014/0259604 A1* | 9/2014 | Romano | ............ | A61B 8/4422 |
| | | | | 29/281.1 |
| 2015/0245822 A1* | 9/2015 | Kim | ............ | A61B 8/4281 |
| | | | | 600/472 |
| 2015/0320387 A1* | 11/2015 | Kubota | ............ | A61B 8/42 |
| | | | | 600/459 |
| 2016/0199027 A1* | 7/2016 | Scully | ............ | A61B 8/4281 |
| | | | | 424/9.5 |
| 2016/0331344 A1* | 11/2016 | Hadzic | ............ | A61B 8/085 |
| 2016/0338665 A1* | 11/2016 | Kitamura | ............ | A61B 8/4422 |
| 2017/0128042 A1* | 5/2017 | Desai | ............ | A61B 8/4281 |
| 2017/0303894 A1* | 10/2017 | Scully | ............ | A61B 8/4422 |
| 2018/0310912 A1* | 11/2018 | Nordgren | ............ | A61L 31/10 |
| 2019/0374198 A1* | 12/2019 | Mullen | ............ | A61B 50/30 |
| 2020/0383660 A1* | 12/2020 | Rothberg | ............ | A61B 8/4281 |

OTHER PUBLICATIONS

English language translation of WO 2020/009395 A1, Copyright © 2022 Clarivate Analytics. (Year: 2022).*
English language translation of CN 107616813 A, Copyright © 2022 Clarivate Analytics. (Year: 2022).*

* cited by examiner

PROBE HEAD-COVER APPLICATOR AND METHOD THEREOF

PRIORITY

This application claims the benefit of priority to U.S. Provisional Application No. 62/894,516, filed Aug. 30, 2019, which is incorporated by reference in its entirety into this application.

BACKGROUND

When following aseptic technique for intravenous ("IV") or midline catheter insertion, probe heads of ultrasound probes are often covered by hand with IV dressings before use on patients. When covering a probe head with an IV dressing by hand, air is commonly unintentionally trapped between the probe head and the IV dressing. The trapped air interferes with ultrasound-image quality, but it is difficult to avoid trapping air when covering a probe head with an IV dressing. It is also difficult to remove the trapped air once trapped between the probe head and the IV dressing. In addition, IV dressings are not designed for covering probe heads. When covering a probe head with an IV dressing by hand, wadding of the IV dressing often occurs by way of overlapping portions of the IV dressing. Such IV-dressing wadding also interferes with ultrasound-image quality.

Disclosed herein is a probe head-cover applicator and method thereof that addresses the foregoing.

SUMMARY

Disclosed herein is a probe head-cover applicator including, in some embodiments, a tray including a cavity, an insert of a compressible material suspended over the cavity, and a probe-head cover adhered to the insert. The insert includes a first adhesive on an outward-facing surface of the insert facing away from the cavity. The probe-head cover is adhered to the insert by the first adhesive. The probe-head cover includes a second adhesive on an outward-facing surface of the probe-head cover facing away from the insert. The second adhesive is configured to adhere the probe-head cover to a probe head of an ultrasound probe when the probe head is inserted into the cavity.

In some embodiments, the cavity is sized to accommodate the probe head together with a combination of the insert and the probe-head cover over the probe head.

In some embodiments, the tray includes major-side openings in major sides of the tray and minor-side openings in minor sides of the tray. The major-side openings and minor-side openings are configured to accommodate therein projections of the insert in support of suspending the insert over the cavity.

In some embodiments, the tray includes a rim around the cavity projecting away from the cavity. The rim is configured for handling the probe head-cover applicator.

In some embodiments, the rim includes at least one gap in the rim configured to accommodate a built-in needle-guide attachment feature of the probe head when the probe head is inserted into the cavity.

In some embodiments, the insert includes longitudinal projections and transverse projections in support of suspending the insert over the cavity.

In some embodiments, the longitudinal projections and transverse projections are configured to facilitate covering the probe head with the insert without overlapping portions of the insert.

In some embodiments, the probe-head cover includes longitudinal projections and transverse projections configured to facilitate covering the probe head with the probe-head cover without overlapping portions of the probe-head cover.

In some embodiments, the first adhesive is disposed in a bead around a perimeter of the outward-facing surface of the insert.

In some embodiments, the probe-head cover is a plastic film.

In some embodiments, the probe-head cover includes an antimicrobial hydrophilic coating on an inward-facing surface of the probe-head cover facing the insert.

In some embodiments, the second adhesive is an ultrasound-transmitting adhesive disposed over an entirety of the outward-facing surface of the probe-head cover.

In some embodiments, the second adhesive has a greater adhesive strength for the probe head than that of the first adhesive for the probe-head cover.

In some embodiments, the insert is configured to compress upon inserting the probe head into the cavity and force out any air trapped between the probe-head cover and the probe head.

Also disclosed herein is a probe head-cover applicator including, in some embodiments, a tray including a cavity, an insert of a compressible material suspended over the cavity, and a probe-head cover adhered to the insert. The tray includes a bottom, major sides, and minor sides of the tray defining the cavity. The maj or sides include major-side openings and the minor sides include minor-side openings. The insert includes transverse projections and longitudinal projections. The insert is suspended over the cavity by the transverse projections in the major-side openings of the tray and the longitudinal projections of the insert in the minor-side openings of the tray. The insert includes a first adhesive on an outward-facing surface of the insert facing away from the cavity. The probe-head cover is adhered to the insert by the first adhesive. The probe-head cover includes a second adhesive on an outward-facing surface of the probe-head cover facing away from the insert. The second adhesive has a greater adhesive strength for a probe head of an ultrasound probe than that of the first adhesive for the probe-head cover. When the probe head is inserted into the cavity to adhere the probe-head cover to the probe head and subsequently withdrawn from the cavity, the probe-head cover remains adhered to the probe head instead of the insert.

In some embodiments, the insert is configured to compress upon inserting the probe head into the cavity and force out any air trapped between the probe-head cover and the probe head.

Also disclosed herein is a method for applying a probe-head cover to a probe head of an ultrasound probe including, in some embodiments, a step of obtaining a probe head-cover applicator. The probe head-cover applicator includes a tray having a cavity defined by a bottom, major sides, and minor sides of the tray, an insert of a compressible material suspended over the cavity, and the probe-head cover adhered to the insert by a first adhesive. Another step of the method includes inserting the probe head into the cavity. The bottom, maj or sides, and minor sides of the tray cause the probe-head cover to contact the probe head, thereby adhering the probe-head cover to the probe head by way of a second adhesive on an outward-facing surface of the probe-head cover facing away from the insert. Another step of the method includes withdrawing the probe head from the cavity, thereby separating the probe-head cover from the insert.

In some embodiments, inserting the probe head into the cavity includes compressing the insert against the bottom, major sides, and minor sides of the tray, which forces out any air trapped between the probe-head cover and the probe head.

In some embodiments, the tray includes major-side openings in the major sides of the tray and minor-side openings in the minor sides of the tray. The major-side openings and minor-side openings are configured to respectively retain therein transverse projections and longitudinal projections of the insert when withdrawing the probe head from the cavity and separating the probe-head cover from the insert.

In some embodiments, the method further includes removing a backing from the outward-facing surface of the probe-head cover to expose the second adhesive before inserting the probe head into the cavity.

In some embodiments, the method further includes opening a package including the probe head-cover applicator, as well as removing the probe head-cover applicator from the package.

Also disclosed herein is a probe head-covering device including, in some embodiments, a substrate of a compressible material and a probe-head cover adhered to the substrate. The substrate includes a first adhesive on a surface of the substrate. The probe-head cover is adhered to the substrate by the first adhesive. The probe-head cover includes a second adhesive on an outward-facing surface of the probe-head cover facing away from the substrate. The second adhesive is configured to adhere the probe-head cover to a probe head of an ultrasound probe.

In some embodiments, the substrate includes longitudinal projections and transverse projections configured to facilitate covering the probe head with the substrate without overlapping portions of the substrate.

In some embodiments, the probe-head cover includes longitudinal projections and transverse projections configured to facilitate covering the probe head with the probe-head cover without overlapping portions of the probe-head cover.

In some embodiments, the first adhesive is disposed in a bead around a perimeter of the surface of the substrate.

In some embodiments, the probe-head cover is a plastic film.

In some embodiments, the probe-head cover includes an antimicrobial hydrophilic coating on a substrate-facing surface of the probe-head.

In some embodiments, the second adhesive is an ultrasound-transmitting adhesive disposed over an entirety of the outward-facing surface of the probe-head cover.

In some embodiments, the second adhesive has a greater adhesive strength for the probe head than that of the first adhesive for the probe-head cover.

Also disclosed herein is a method for applying a probe-head cover to a probe head of an ultrasound probe including, in some embodiments, a step of obtaining a probe head-covering device. The probe head-covering device includes a substrate of a compressible material including a first adhesive on a surface of the substrate. The probe head-covering device also includes a probe-head cover adhered to the substrate by the first adhesive. The probe-head cover includes a second adhesive on an outward-facing surface of the probe-head cover facing away from the substrate. Another step of the method includes contacting the probe head with the probe-head cover causing at least a medial portion of the probe-head cover to adhere to the probe head by way of the second adhesive. Another step of the method includes pushing transverse projections and longitudinal projections of the probe head-covering device over corresponding sides of the probe head to adhere a remainder of the probe-head cover to the probe head. Another step of the method includes allowing the substrate to flatten out and separating the probe-head cover from the substrate.

In some embodiments, pushing the transverse projections and the longitudinal projections of the probe head-covering device over the corresponding sides of the probe head forces out any air trapped between the probe-head cover and the probe head.

In some embodiments, the method further includes removing a backing from the outward-facing surface of the probe-head cover to expose the second adhesive before contacting the probe head with the probe-head cover.

In some embodiments, the method further includes opening a package including the probe head-covering device and removing the probe head-covering device from the package.

These and other features of the concepts provided herein will become more apparent to those of skill in the art in view of the accompanying drawings and following description, which describe particular embodiments of such concepts in greater detail.

DRAWINGS

DESCRIPTION

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

Unless defined otherwise, all technical and scientific terms used herein have the same meaning as commonly understood by those of ordinary skill in the art.

As set forth above, air is commonly unintentionally trapped between a probe head of an ultrasound probe and an IV dressing when covering the probe head with an IV dressing by hand. Wadding of the IV dressing also often occurs by way of overlapping portions of the IV dressing when covering a probe head with an IV dressing by hand. The trapped air and the wadding of the IV dressing interfere with ultrasound-image quality, so a probe-head applicator and method thereof is needed to address the foregoing.

Probe Head-Cover Applicator

Figure 1:
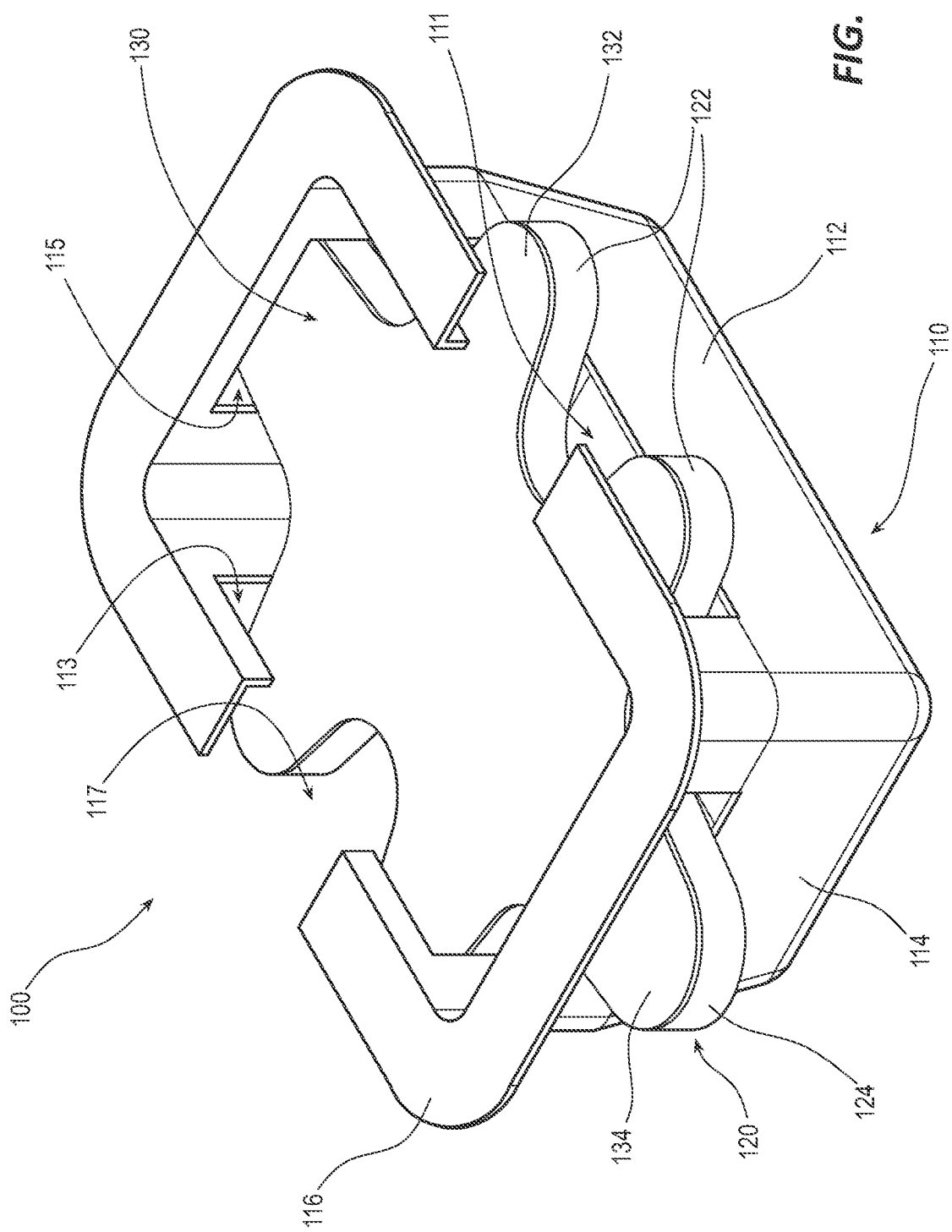
FIG. 1 illustrates a probe head-cover applicator in accordance with some embodiments.

FIG. 1 illustrates a probe head-cover applicator 100 in accordance with some embodiments.

As shown, the probe head-cover applicator 100 includes, in some embodiments, a tray 110 including a cavity 111, an insert 120 of a compressible material suspended over the cavity 111, and a probe-head cover 130 adhered to the insert 120.

The tray 110 includes a bottom, major sides 112, and minor sides 114 defining the cavity 111. The cavity 111 of the tray 110 is sized to accommodate a probe head of an ultrasound probe together with a combination of the insert 120 and the probe-head cover 130 over the probe head. (See FIG. 2, where the probe head is inserted into the cavity 111 with the insert 120 and the probe-head cover 130 between the probe head and the tray 110.)

The tray 110 includes major-side openings 113 in the major sides 112 of the tray 110 and minor-side openings 115 in the minor sides 114 of the tray 110. The major-side openings 113 and the minor-side openings 115 are configured to accommodate therein projections of the insert 120 in support of suspending the insert 120 over the cavity 111 of the tray 110 by the projections. As set forth below, the projections of the insert 120 are the transverse projections 122 and the longitudinal projections 124 of the insert 120. The major-side openings 113 and the minor-side openings 115 of the tray 110 are respectively configured to accommodate therein the transverse projections 122 and the longitudinal projections 124 of the insert 120 in support of suspending the insert 120 over the cavity 111 of the tray 110. However, the tray 110 is not limited to the major-side openings 113 or the minor-side openings 115 for the foregoing functionality. Indeed, the major-side openings 113 can alternatively be major-side recesses or pockets and, independently, the minor-side openings 115 can alternatively be minor-side recesses or pockets.

The tray 110 includes a rim 116 around the cavity 111 of the tray 110 for handling the probe head-cover applicator 100. The rim 116 projects away from the cavity 111 and can include at least one gap 117 in the rim 116 configured to accommodate a built-in needle-guide attachment feature of a probe head of an ultrasound probe when the probe head is inserted into the cavity 111 of the tray 110. (See FIG. 2, where the gap 117 in the rim 116 accommodates a built-in needle-guide attachment feature of a probe head.) Indeed, the rim 116 can include two gaps in the rim 116 with each gap of the two gaps in one of the major sides 112 of the tray 110. When present, each gap in the rim 116 extends into the major opening on its major side of the tray 110. While only one gap of the two gaps in the rim 116 is needed to accommodate a built-in needle-guide attachment feature of a probe head, the two gaps in the rim 116 of the tray 110 result in a symmetrical tray that facilitates using the probe head-cover applicator 100. Indeed, twofold rotational symmetry of the entire probe head-cover applicator 100 facilitates using the probe head-cover applicator 100 in that users need not line up a particular major side of a probe head (e.g., the major side of the probe head including the built-in needle-guide attachment feature) to a particular major side of the tray 110 (e.g., the major side of the probe head including the gap 117 in the rim 116). Instead, only lining up major sides of the probe head to the major sides 112 of the tray 110 is required, thereby simplifying use of the probe head-cover applicator 100.

The insert 120 includes the transverse projections 122 and the longitudinal projections 124 in support of suspending the insert 120 over the cavity 111 of the tray 110. Like the rim 116 of the tray 110, the transverse projections 122 on any given side of the major sides 112 of the tray 110 include a gap between the transverse projections 122 to accommodate a built-in needle-guide attachment feature of a probe head of an ultrasound probe when the probe head is inserted into the cavity 111 of the tray 110. (See FIG. 2, where the gap between the transverse projections 122 accommodates a built-in needle-guide attachment feature of a probe head.) The transverse projections 122 and the longitudinal projections 124 are configured to facilitate covering a probe head of an ultrasound probe with the insert 120 without overlapping portions or wadding of the insert 120.

The insert 120 includes a compressible material such as a foam, a rubber (e.g., silicone rubber), or the like. The insert 120 is configured with a certain thickness (e.g., ⅛") such that the insert 120 compresses upon inserting a probe head of an ultrasound probe into the cavity 111 of the tray 110, thereby form-fitting the probe head. As the insert 120 form-fits the probe head, the insert 120 simultaneously forces out any air trapped between the probe-head cover 130 and the probe head. Mechanistically, the insert 120 rolls out any air trapped between the probe-head cover 130 and the probe head starting at an apex of the probe head, continuing over a remainder of convex portions of the probe head, and finally over major and minor sides of the probe head as such portions of the probe head are inserted into the cavity 111 of the tray 110. Depending upon the compressible material (e.g., foam), the insert 120 is inclined to recover an original shape of the insert 120 upon withdrawing the probe head of the ultrasound probe from the cavity 111 of the tray 110, which automatically separates the probe-head cover 130 from the probe head.

The insert 120 includes a first adhesive on an outward-facing surface of the insert 120 facing away from the cavity 111 or the tray 110 configured for adhering the probe-head cover 130 to the insert 120. While not shown, the first adhesive can be disposed in a bead around a perimeter of the outward-facing surface of the insert 120. The perimeter incudes an outer perimeter of the insert 120 or a scanning-window perimeter within the outer perimeter. The scanning-window perimeter corresponds to where a scanning window of a probe head of an ultrasound probe is ultimately placed over the insert 120. That said, the first adhesive can alternatively be disposed over an entirety of the outward-facing surface of the insert 120.

The probe-head cover 130 is a plastic film (e.g., polyurethane) including transverse projections 132 and longitudinal projections 134 configured to facilitate covering a probe head of an ultrasound probe with the probe-head cover 130 without overlapping portions or wadding of the probe-head cover 130. The transverse projections 132 and the longitudinal projections 134 generally match those of the insert 120 such that that the transverse projections 132 and the longitudinal projections 134 of the probe-head cover 130 are supported by those of the insert 120. Like the insert 120, the transverse projections 132 on any given side of the major sides 112 of the tray 110 include a gap between the transverse projections 132 to accommodate a built-in needle-guide attachment feature of a probe head when the probe head is inserted into the cavity 111 of the tray 110. (See FIG.

2, where the gap between the transverse projections 132 accommodates a built-in needle-guide attachment feature of a probe head.)

The probe-head cover 130 includes a second adhesive (e.g., an ultrasound-transmitting adhesive such as a silicone adhesive) disposed over an entirety of on an outward-facing surface of the probe-head cover 130 facing away from the insert 120. (Again, the probe-head cover 130 is adhered to the insert 120 by the first adhesive.) The second adhesive is configured to adhere the probe-head cover 130 to a probe head of an ultrasound probe when the probe head is inserted into the cavity 111 of the tray 110 with a combination of the insert 120 and the probe-head cover 130 between the probe head and the tray 110. The second adhesive has a greater adhesive strength for the probe head than that of the first adhesive for the probe-head cover 130. In other words, the second adhesive is configured to adhere the probe-head cover 130 to the probe head more strongly than the first adhesive adheres the probe-head cover 130 to the insert 120. This allows the probe-head cover 130 to selectively pull away from the insert 120 when the probe head is withdrawn from the cavity 111 of the probe head-cover applicator 100. That is, when the probe head is inserted into the cavity 111 of the tray 110 to adhere the probe-head cover 130 to the probe head and subsequently withdrawn from the cavity 111, the probe-head cover 130 remains adhered to the probe head instead of the insert 120. None of the first adhesive on the outward-facing surface of the insert 120 transfers to the probe-head cover 130 upon withdrawing the probe head from the cavity 111 of the probe head-cover applicator 100.

The probe-head cover 130 includes an antimicrobial hydrophilic coating on an inward-facing surface of the probe-head cover 130 facing the insert 120. The inward-facing surface of the probe-head cover 130 in the probe head-cover applicator 100 becomes a skin-contacting surface of the probe-head cover 130 upon adhering the probe-head cover 130 to a probe head of an ultrasound probe.

In addition to mitigating issues with wadding of a probe-head cover such as an IV dressing and trapping air between a probe head of an ultrasound probe and the IV dressing, the probe-head applicator 100 and method thereof enable probe-head covers such as the probe-head cover 130 to be applied to probe heads without touching the probe-head covers by hand. This is notable in that touching a probe-head cover such as an IV dressing can degrade the adhesive of the IV dressing used to stick to the IV dressing to a probe head. In addition, touching a probe-head cover such as an IV dressing can contaminate the IV dressing. Use of the antimicrobial hydrophilic coating on the inward-facing surface of the probe-head cover 130 combined with not needing to touch the probe-head cover 130 enhances sterility during vein or arterial cannulation.

Probe Head-Covering Device

While not separately shown, a probe head-covering device includes the insert 120 and the probe-head cover 130 of the probe head-cover applicator 100; however, the probe head-covering device excludes the tray 110 of the probe head-cover applicator 100. Since the probe head-covering device excludes the tray 110, the insert 120 is referred to as the substrate 120 when describing the probe head-covering device. This is because the substrate 120 need not be inserted in the tray 110 and suspended over the cavity 111 of the tray 110. It should be understood the description set forth herein for the insert 120 of the probe head-cover applicator 100 generally applies to the substrate 120 of the probe head-covering device. Likewise, the description set forth herein for the probe-head cover 130 of the probe head-cover applicator 100 generally applies to the probe-head cover 130 of the probe head-covering device.

The probe head-covering device includes, in some embodiments, the substrate 120 of the compressible material and the probe-head cover 130 adhered to the substrate 120. The substrate 120 includes the first adhesive on a surface of the substrate 120. The probe-head cover 130 is adhered to the substrate 120 by the first adhesive. The probe-head cover 130 includes the second adhesive on the outward-facing surface of the probe-head cover 130 facing away from the substrate 120. The second adhesive is configured to adhere the probe-head cover 130 to a probe head of an ultrasound probe.

The substrate 120 includes the transverse projections 122 and the longitudinal projections 124 configured to facilitate covering the probe head with the substrate 120 without overlapping portions of the substrate 120. Likewise, the probe-head cover 130 includes the transverse projections 132 and the longitudinal projections 134 configured to facilitate covering the probe head with the probe-head cover without overlapping portions of the probe-head cover 130. Because the substrate 120 and the probe-head cover 130 need not be suspended over the cavity 111 of the tray 110, the transverse projections 122 and 132 and the longitudinal projections 124 and 134 can be different than those set forth for the insert 120 and the probe-head cover 130 of the probe head-cover applicator 100. For example, instead of a pair of the transverse projections 122 and 132 on each major side of the probe head-covering device, the probe head-covering device can include a single transverse projection on each major side of the probe head-covering device.

For additional details for the substrate 120 and the probe-head cover 130 of the probe head-covering device, see the description set forth herein for the insert 120 and the probe-head dover 130 of the probe head-cover applicator 100.

Methods

Figure 2:
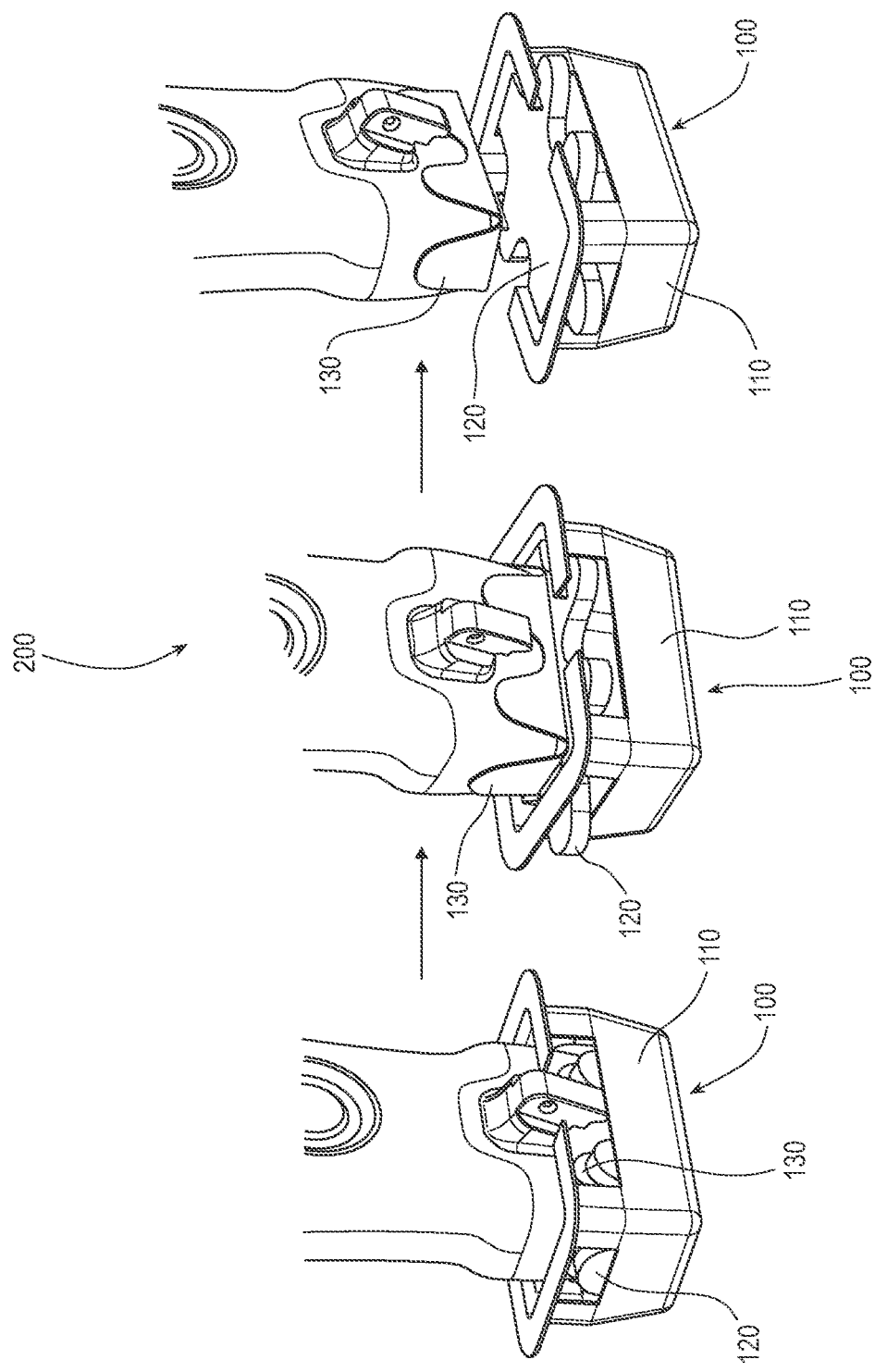
FIG. 2 illustrates a portion of a method of the probe head-cover applicator in accordance with some embodiments.

FIG. 2 illustrates a portion of a method 200 for applying the probe-head cover 130 to a probe head of an ultrasound probe with the probe head-cover applicator 100 in accordance with some embodiments.

The method 200 includes a step of obtaining the probe head-cover applicator 100, which includes the tray 110 having the cavity 111 defined by the bottom, the major sides 112, and the minor sides 114 of the tray 110, the insert 120 suspended over the cavity 111, and the probe-head cover 130 adhered to the insert 120 by the first adhesive. The method can further include opening a package including the probe head-cover applicator 100 once the probe head-cover applicator 100 or the package thereof is obtained, as well as removing the probe head-cover applicator 100 from the package.

Another step of the method 200 includes inserting the probe head of the ultrasound probe into the cavity 111 of the tray 110 as shown in FIG. 2. The bottom, the major sides 112, and the minor sides 114 of the tray 110 cause the probe-head cover 130 to contact the probe head, thereby adhering the probe-head cover 130 to the probe head by way of the second adhesive on the outward-facing surface of the probe-head cover 130 facing away from the insert 120. Inserting the probe head into the cavity 111 includes compressing the insert 120 against the bottom, the major sides 112, and the minor sides 114 of the tray 110, which forces out any air trapped between the probe-head cover 130 and the probe head. Mechanistically, inserting the probe head into the cavity 111 rolls out any air trapped between the probe-head cover 130 and the probe head starting at the apex of the probe head, continuing over the remainder of the convex portions of the probe head, and finally the major and minor sides of the probe head as such portions of the probe head are inserted into the cavity 111 of the tray 110.

Another step of the method 200 includes removing a backing from the outward-facing surface of the probe-head cover 130 to expose the second adhesive before inserting the probe head into the cavity. Removing the backing from the outward-facing surface of the probe-head cover 130 can be done while unpackaging the probe head-cover applicator 100.

Another step of the method 200 includes withdrawing the probe head from the cavity 111 of the tray 110 as shown in FIG. 2, thereby separating the probe-head cover 130 from the insert 120. Again, the tray 110 includes the major-side openings 113 in the major sides 112 of the tray 110 and the minor-side openings 115 in the minor sides 114 of the tray 110. The major-side openings 113 and the minor-side openings 115 are configured to respectively retain therein the transverse projections 122 and the longitudinal projections 124 of the insert 120 when withdrawing the probe head from the cavity 111 of the tray 110 and separating the probe-head cover 130 from the insert 120.

While not separately shown, a method for applying the probe-head cover 130 to a probe head of an ultrasound probe with the probe head-covering device includes a step of obtaining the probe head-covering device. The method can further include opening a package including the probe head-covering device once the probe head-covering device or the package thereof is obtained, as well as removing the probe head-covering device from the package.

Another step of the method includes removing a backing from the outward-facing surface of the probe-head cover 130 to expose the second adhesive before contacting the probe head with the probe-head cover 130. Removing the backing from the outward-facing surface of the probe-head cover 130 can be done while unpackaging the probe head-covering device.

Another step of the method includes contacting the probe head with the probe-head cover 130 causing at least a medial portion of the probe-head cover 130 to adhere to the probe head by way of the second adhesive.

Another step of the method includes pushing the transverse projections 122 and 132 and the longitudinal projections 124 and 134 of the probe head-covering device over corresponding sides of the probe head to adhere a remainder of the probe-head cover 130 to the probe head. Pushing the transverse projections 122 and 132 and the longitudinal projections 124 and 134 of the probe head-covering device over the corresponding sides of the probe head forces out any air trapped between the probe-head cover 130 and the probe head.

Another step of the method includes allowing the substrate 120 to flatten out followed by separating the probe-head cover 130 from the substrate 120.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. A probe head-cover applicator, comprising:
a tray including a cavity;
an insert of a compressible material suspended over the cavity, the insert including a first adhesive on an outward-facing surface of the insert facing away from the cavity; and
a probe-head cover adhered to the insert by the first adhesive, the probe-head cover including a second adhesive on an outward-facing surface of the probe-head cover facing away from the insert configured to adhere the probe-head cover to a probe head of an ultrasound probe when the probe head is inserted into the cavity.

2. The probe head-cover applicator of claim 1, wherein the cavity is sized to accommodate the probe head together with a combination of the insert and the probe-head cover over the probe head.

3. The probe head-cover applicator of claim 1, wherein the tray includes major-side openings in major sides of the tray and minor-side openings in minor sides of the tray, the major-side openings and minor-side openings configured to accommodate therein projections of the insert in support of suspending the insert over the cavity.

4. The probe head-cover applicator of claim 1, wherein the tray includes a rim around the cavity projecting away from the cavity, the rim configured for handling the probe head-cover applicator.

5. The probe head-cover applicator of claim 4, wherein the rim includes at least one gap in the rim configured to accommodate a built-in needle-guide attachment feature of the probe head when the probe head is inserted into the cavity.

6. The probe head-cover applicator of claim 1, wherein the insert includes longitudinal projections and transverse projections in support of suspending the insert over the cavity.

7. The probe head-cover applicator of claim 6, wherein the longitudinal projections and transverse projections are configured to facilitate covering the probe head with the insert without overlapping portions of the insert.

8. The probe head-cover applicator of claim 1, wherein the probe-head cover includes longitudinal projections and transverse projections configured to facilitate covering the probe head with the probe-head cover without overlapping portions of the probe-head cover.

9. The probe head-cover applicator of claim 1, wherein the first adhesive is disposed in a bead around a perimeter of the outward-facing surface of the insert.

10. The probe head-cover applicator of claim 1, wherein the probe-head cover is a plastic film.

11. The probe head-cover applicator of claim 1, wherein the probe-head cover includes an antimicrobial hydrophilic coating on an inward-facing surface of the probe-head cover facing the insert.

12. The probe head-cover applicator of claim 1, wherein the second adhesive is an ultrasound-transmitting adhesive disposed over an entirety of the outward-facing surface of the probe-head cover.

13. The probe head-cover applicator of claim 1, wherein the second adhesive has a greater adhesive strength for the probe head than that of the first adhesive for the probe-head cover.

14. The probe head-cover applicator of claim 1, wherein the insert is configured to compress upon inserting the probe head into the cavity and force out any air trapped between the probe-head cover and the probe head.

15. A probe head-cover applicator, comprising:
a tray including a cavity defined by a bottom, major sides, and minor sides of the tray, the major sides including major-side openings and the minor sides including minor-side openings;
an insert of a compressible material suspended over the cavity by transverse projections of the insert in the major-side openings of the tray and longitudinal projections of the insert in the minor-side openings of the tray, the insert including a first adhesive on an outward-facing surface of the insert facing away from the cavity; and
a probe-head cover adhered to the insert by the first adhesive, the probe-head cover including a second adhesive on an outward-facing surface of the probe-head cover facing away from the insert having a greater adhesive strength for a probe head of an ultrasound probe than that of the first adhesive for the probe-head cover such that when the probe head is inserted into the cavity to adhere the probe-head cover to the probe head and subsequently withdrawn from the cavity, the probe-head cover remains adhered to the probe head instead of the insert.

16. The probe head-cover applicator of claim 15, wherein the insert is configured to compress upon inserting the probe head into the cavity and force out any air trapped between the probe-head cover and the probe head.

17. A method for applying a probe-head cover to a probe head of an ultrasound probe, comprising:
obtaining a probe head-cover applicator, the probe head-cover applicator including:
a tray including a cavity defined by a bottom, major sides, and minor sides of the tray; and
an insert of a compressible material suspended over the cavity, wherein the probe-head cover is adhered to the insert by a first adhesive;
inserting the probe head into the cavity, the bottom, major sides, and minor sides of the tray causing the probe-head cover to contact the probe head, thereby adhering the probe-head cover to the probe head by way of a second adhesive on an outward-facing surface of the probe-head cover facing away from the insert; and
withdrawing the probe head from the cavity, thereby separating the probe-head cover from the insert.

18. The method of claim 17, wherein inserting the probe head into the cavity includes compressing the insert against the bottom, major sides, and minor sides of the tray and forcing out any air trapped between the probe-head cover and the probe head.

19. The method of claim 17, wherein the tray includes major-side openings in the major sides of the tray and minor-side openings in the minor sides of the tray, the major-side openings and minor-side openings configured to respectively retain therein transverse projections and longitudinal projections of the insert when withdrawing the probe head from the cavity and separating the probe-head cover from the insert.

20. The method of claim 17, further comprising removing a backing from the outward-facing surface of the probe-head cover to expose the second adhesive before inserting the probe head into the cavity.

21. The method of claim 17, further comprising:
opening a package including the probe head-cover applicator; and
removing the probe head-cover applicator from the package.

* * * * *